US009791589B2

(12) United States Patent
Chen et al.

(10) Patent No.: US 9,791,589 B2
(45) Date of Patent: Oct. 17, 2017

(54) DOWNHOLE DIFFERENTIATION OF LIGHT OIL AND OIL-BASED FILTRATES BY NMR WITH OLEOPHILIC NANOPARTICLES

(71) Applicant: Halliburton Energy Services, Inc., Houston, TX (US)

(72) Inventors: Songhua Chen, Katy, TX (US); Ronald E. Cherry, Humble, TX (US); Magdalena Sandor, Humble, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 794 days.

(21) Appl. No.: 14/237,898

(22) PCT Filed: Mar. 1, 2013

(86) PCT No.: PCT/US2013/028545
§ 371 (c)(1),
(2) Date: Feb. 10, 2014

(87) PCT Pub. No.: WO2014/133537
PCT Pub. Date: Sep. 4, 2014

(65) Prior Publication Data
US 2015/0212227 A1    Jul. 30, 2015

(51) Int. Cl.
*G01V 3/32* (2006.01)
*G01V 3/34* (2006.01)
(Continued)

(52) U.S. Cl.
CPC ............... *G01V 3/32* (2013.01); *G01V 3/34* (2013.01); *G01V 3/38* (2013.01); *G01N 24/081* (2013.01)

(58) Field of Classification Search
CPC .......... G01V 3/32; G01V 3/38; G01N 24/081; G01R 33/3808; G01R 33/448
(Continued)

(56) References Cited

U.S. PATENT DOCUMENTS 8,168,570 B2    5/2012    Barron et al.
8,269,501 B2    9/2012    Schmidt et al.
(Continued)

FOREIGN PATENT DOCUMENTS

WO    2011063023    5/2011
WO    2011094275    8/2011
(Continued)

OTHER PUBLICATIONS

Horkowitz et al., "Residual Oil Saturation Measurements in Carbonates with Pulsed NMR Logs," SPWLA Symposium Paper Q, 1995.
(Continued)

*Primary Examiner* — Walter L Lindsay, Jr.
*Assistant Examiner* — Frederick Wenderoth
(74) *Attorney, Agent, or Firm* — McDermott Will & Emery LLP

(57) ABSTRACT

Downhole nuclear magnetic resonance (NMR) methods that utilize oleophilic nanoparticle may allow for differentiation of light oil and oil-based filtrates. For example, a method may involve drilling a wellbore penetrating a subterranean formation using an oil-based drilling fluid that comprises an oil base fluid and a plurality of oleophilic nanoparticles; performing a plurality of NMR measurements at a plurality of depths of investigation (DOI) of a near-wellbore portion of the subterranean formation; and producing an invasion profile of an oil-based drilling fluid filtrate into the near-wellbore portion of the subterranean formation based on the plurality of NMR measurements.

20 Claims, 3 Drawing Sheets

(51) Int. Cl.
  *G01V 3/38*   (2006.01)
  *G01N 24/08*  (2006.01)
(58) Field of Classification Search
  USPC .......................................................... 324/303
  See application file for complete search history.

(56) References Cited

U.S. PATENT DOCUMENTS

| | | | |
|---|---|---|---|
| 8,701,774 | B2 | 4/2014 | Johnson, Sr. |
| 2003/0052674 | A1 | 3/2003 | Speier et al. |
| 2004/0104048 | A1* | 6/2004 | Woodburn ............... G01V 3/32 175/50 |
| 2004/0104341 | A1* | 6/2004 | Betancourt ............. E21B 47/10 250/255 |
| 2004/0225441 | A1 | 11/2004 | Tilke et al. |
| 2005/0119725 | A1* | 6/2005 | Wang ....................... A61F 2/82 623/1.15 |
| 2010/0264915 | A1 | 10/2010 | Saldungaray et al. |
| 2011/0181278 | A1 | 7/2011 | Chen et al. |
| 2011/0297394 | A1* | 12/2011 | VanDelden ............. E21B 33/06 166/373 |
| 2012/0000641 | A1 | 1/2012 | Panga et al. |
| 2012/0015852 | A1 | 1/2012 | Quintero et al. |
| 2012/0024527 | A1* | 2/2012 | Tarafdar .................. C04B 24/32 166/293 |
| 2012/0067577 | A1 | 3/2012 | Roddy |
| 2012/0068700 | A1 | 3/2012 | Chen et al. |
| 2012/0145401 | A1* | 6/2012 | Reyes ...................... C09K 8/78 166/305.1 |
| 2012/0202047 | A1 | 8/2012 | Welch et al. |
| 2012/0211227 | A1 | 8/2012 | Thaemlitz et al. |
| 2012/0234533 | A1 | 9/2012 | Chen |
| 2012/0318510 | A1 | 12/2012 | Ocalan |
| 2012/0325472 | A1 | 12/2012 | Litvinets et al. |
| 2013/0092828 | A1 | 4/2013 | Perna et al. |
| 2013/0342205 | A1* | 12/2013 | Prado ..................... G01N 24/08 324/309 |
| 2014/0041862 | A1 | 2/2014 | Ersoz |
| 2014/0145716 | A1 | 5/2014 | Dirksen et al. |
| 2015/0145512 | A1 | 5/2015 | Chen et al. |
| 2015/0212227 | A1 | 7/2015 | Chen et al. |
| 2015/0368541 | A1 | 12/2015 | Monclin et al. |

FOREIGN PATENT DOCUMENTS

| | | |
|---|---|---|
| WO | 2011133859 A1 | 10/2011 |
| WO | 2012091599 | 7/2012 |
| WO | 2014133537 A1 | 9/2014 |

OTHER PUBLICATIONS

International Search Report and Written Opinion for PCT/US2013/028545 dated Nov. 6, 2013.
Morales et al., Magnetic Studies of Iron Oxide Nanoparticles Coated with Oleic Acid and Pluronic® Block Copolymer, Journal of Applied Physics 97, 10Q905 (2005).

* cited by examiner

DOWNHOLE DIFFERENTIATION OF LIGHT OIL AND OIL-BASED FILTRATES BY NMR WITH OLEOPHILIC NANOPARTICLES

BACKGROUND

The compositions and methods described herein relate to the downhole differentiation of light oil and oil-based filtrates by nuclear magnetic resonance (NMR) methods using oleophilic nanoparticles.

In oil and gas exploration it is desirable to understand the structure and properties of the subterranean formation surrounding a wellbore, in order to determine if the formation contains hydrocarbon resources (oil and/or gas), to estimate the amount and producibility of hydrocarbon contained in the formation, and to evaluate the completion operation parameters for bringing the wellbore into production. A significant tool in this evaluation is the use of wireline logging and/or logging-while-drilling (LWD) or measurement-while-drilling (MWD) for analyzing the near-wellbore formation and near-wellbore fluids. Typically, one or more logging tools are lowered into the wellbore and the tool readings or measurement logs are recorded as the tools traverse the wellbore. These measurement logs are used to infer the properties of the near-wellbore formation and/or the near-wellbore fluids.

Nuclear magnetic resonance (NMR) logging is especially useful for analyzing the composition, viscosity, diffusivity, and location of near-wellbore fluids and the porosity and permeability of the near-wellbore formation, as these relate directly or indirectly to the NMR like spin-density, $T_1$ and the $T_2$ relaxation times, and signal decay rate. NMR logging is based on the observation that when an assembly of magnetic moments, such as those of hydrogen nuclei, are exposed to a static magnetic field, they tend to align along the direction of the magnetic field, resulting in bulk magnetization. The rate at which equilibrium is established in such bulk magnetization is characterized by the parameter $T_1$, known as the spin-lattice relaxation time. The $T_1$ parameter characterizes the coupling of nuclear spins to energy-absorbing molecular motions like rotation, vibration, and translation. Another related and frequently used NMR logging parameter is the spin-spin relaxation time $T_2$ (also known as transverse relaxation time), which is an expression of the relaxation due to non-homogeneities in the local magnetic field over the sensing volume of the logging tool. In general, the mechanisms for spin-spin relaxation time $T_2$ include, in addition to those contributing to $T_1$, the exchange of energy between spins.

For accurate NMR logging, the various materials being queried (e.g., the various formation rock and various fluids therein) need to have NMR parameter values. However, the wellbore fluids utilized in wellbore operations (e.g., drilling operations) can have similar NMR parameter values to near-wellbore fluids. As such, fluid differentiation becomes difficult when wellbore fluids infiltrate the subterranean formation, often referred to as filtrates. When the filtrate and the formation fluid have similar NMR parameter values, the properties of the formation fluid can be skewed by the filtrate. Inaccurate NMR parameter values may lead to inaccurate formation fluid properties and consequently the design of an inefficient wellbore completion operation.

Most often, fluid differentiation can be difficult between filtrates from aqueous wellbore fluids and formation water and between filtrates from oil-based wellbore fluids and light oil in the formation. In some instances, wellbore fluids have been doped with NMR contrast agents like chelated gadolinium to assist in fluid differentiation. However, in aqueous-based wellbore fluids, the concentration of chelated gadolinium needed to achieve adequate contrast is sufficiently high that to achieve such a concentration the ratio of chelant to gadolinium increases to a point that the gadolinium is no longer an effective contrast agent.

Oil-based mud is often chosen for wellbore stability in shale formation, in deep or high-temperature wells that dehydrates water-based mud, or drilling through water-soluble formation such as salt. Oil-base filtrates with NMR parameters similar to that of the oil-based formation fluids can magnify any inaccuracy associated with NMR logging methods. Accordingly, enhancing the ability to differentiate oil-based filtrates and oil-based formation fluids such as light oils is important to identify or quantify the reservoir fluids and fluid saturations.

SUMMARY OF THE INVENTION

The compositions and methods described herein relate to the downhole differentiation of light oil and oil-based filtrates by NMR methods using oleophilic nanoparticles.

In some embodiments, a method may involve drilling a wellbore penetrating a subterranean formation using a oil-based drilling fluid that comprises an oil base fluid and a plurality of oleophilic nanoparticles; performing a plurality of NMR measurements at a plurality of depths of investigation (DOI) of a near-wellbore portion of the subterranean formation; and producing an invasion profile of a oil-based drilling fluid filtrate into the near-wellbore portion of the subterranean formation based on the plurality of NMR measurements.

In other embodiments, a method may involve drilling a wellbore penetrating a subterranean formation using a oil-based drilling fluid that comprises an oil base fluid and a plurality of oleophilic nanoparticles; extracting a plurality of near-wellbore fluid samples from the subterranean formation; measuring an NMR parameter of the near-wellbore fluid samples with an NMR wellbore tool; and collecting the near-wellbore fluid sample comprising an uncontaminated formation fluid.

In yet other embodiments, a method may involve drilling a wellbore penetrating a subterranean formation; measuring a first porosity distribution for the subterranean formation with a first NMR wellbore tool; reaming a wellbore surface to remove a filter cake from the wellbore, thereby yielding a reamed wellbore; introducing a wellbore fluid into the reamed wellbore, the wellbore fluid comprising an oil base fluid and a plurality of oleophilic nanoparticles; measuring a second porosity distribution of the subterranean formation with a second NMR wellbore tool; and determining a vug porosity of the subterranean formation based on a comparison of the first porosity distribution in the second porosity distribution.

In some embodiments, a method may involve drilling a wellbore penetrating a subterranean formation using a oil-based drilling fluid comprising an oil base fluid and a plurality of oleophilic nanoparticles; measuring a first porosity distribution for the subterranean formation with a first NMR wellbore tool; measuring a second porosity distribution of the subterranean formation with a second NMR wellbore tool; and determining a vug porosity of the subterranean formation based on a comparison of the first porosity and the second porosity distributions.

In other embodiments, a method may involve introducing a wellbore fluid into a wellbore penetrating a subterranean formation, the wellbore fluid comprising an oil-based fluid and a plurality of oleophilic nanoparticles; forming a plurality of nanoparticle aggregates between a filter cake and at least a portion of the subterranean formation, the nanoparticle aggregates comprising the oleophilic nanoparticles; performing a plurality of NMR measurements at the portion of the subterranean formation; and determining a vug connectivity based on the plurality of NMR measurements.

In some embodiments, a method may involve introducing a wellbore fluid comprising an oil base fluid and a plurality of oleophilic nanoparticles described herein into a subterranean formation comprising residual oil that comprises light oil; performing NMR measurements on a near-wellbore portion of the subterranean formation; and determining the residual oil saturation based on the NMR measurements.

The features and advantages of the present invention will be readily apparent to those skilled in the art upon a reading of the description of the preferred embodiments that follows.

BRIEF DESCRIPTION OF THE DRAWINGS

The following figures are included to illustrate certain aspects of the present invention, and should not be viewed as exclusive embodiments. The subject matter disclosed is capable of considerable modifications, alterations, combinations, and equivalents in form and function, as will occur to those skilled in the art and having the benefit of this disclosure.

DETAILED DESCRIPTION

Figure 1:
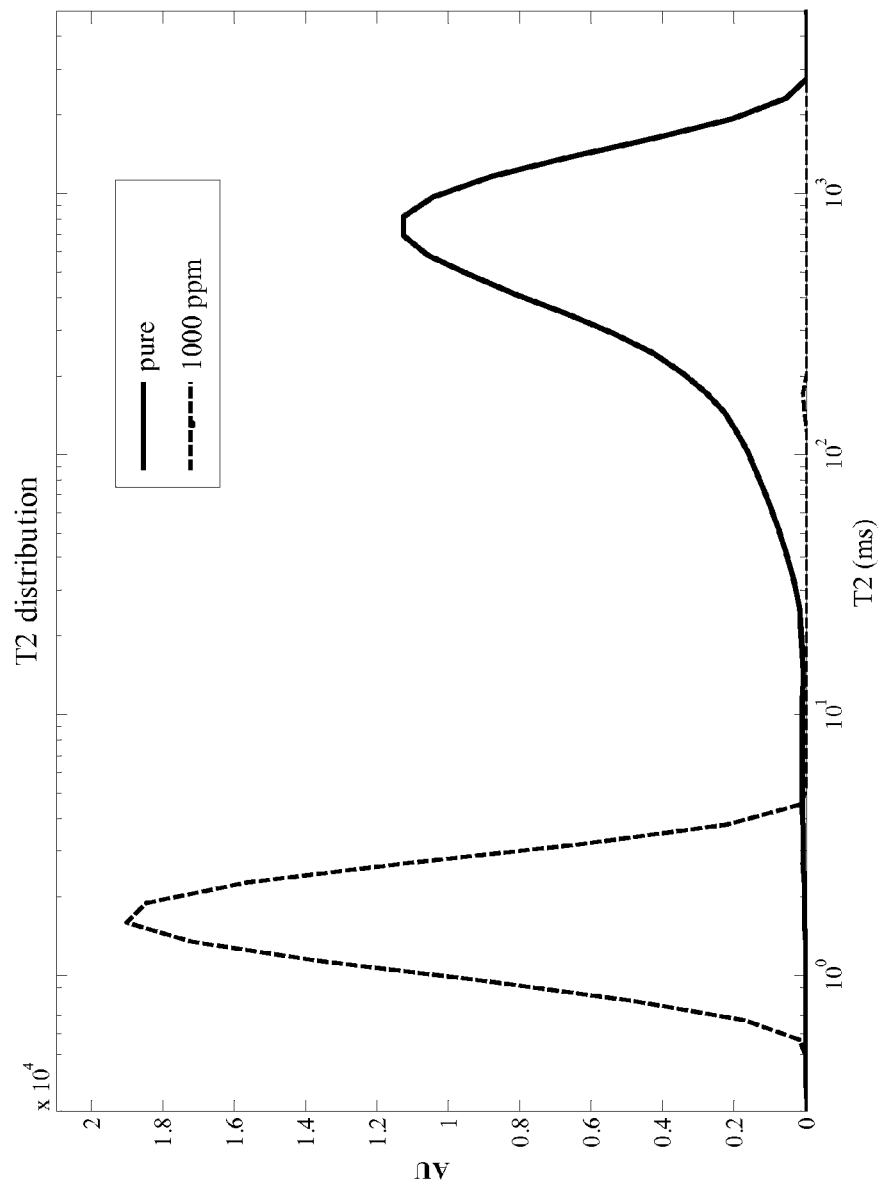
FIG. 1 provides a $T_2$ relaxation time plot for a light oil sample and a light oil sample doped with oleophilic nanoparticles.

The compositions and methods described herein relate to the downhole differentiation of light oil and oil-based filtrates by NMR methods using oleophilic nanoparticles.

The properties of the subterranean formation and/or the formation fluid, especially oil-based formation fluids, may be useful in designing efficient wellbore completion and wellbore production operations. The ability to differentiate light oil from oil-based filtrates may enhance the accuracy of a plurality of methods for ascertaining such properties that utilize NMR techniques downhole. Doping oil-based wellbore fluids with oleophilic nanoparticles described herein may allow for such differentiation by changing the value of a given NMR parameter (e.g., reducing the $T_1$ relaxation time, reducing the $T_2$ relaxation time, and/or parameters relating thereto like spin-density and signal decay rate) of the oil-based wellbore fluid and consequently the oil-based filtrate. As used herein, the term "oleophilic nanoparticle" refers to a nanoparticle having an oleophilic surface modification.

Typically, filtrates infiltrate the near-wellbore formation before and during filter cake formation. The filtrate infiltration is typically through the pores, vugs, microfractures, and fractures of the subterranean formation. Effective contrast between oil-based wellbore fluids (or the filtrates thereof) and oil-based formation fluids like light oil depend on, inter alia, the ability for a contrast agent to travel with the oil-based wellbore fluid as it infiltrates the near-wellbore formation and the ability for a contrast agent to stay suspended for a time period long enough to allow for the NMR measurements. As such, the size of the oleophilic nanoparticles described herein may advantageously allow for unhindered or minimally hindered transport with the oil-based filtrate through each of these infiltration routes. Further, the oleophilic surface modification of the oleophilic nanoparticles may enhance suspension properties and mitigate the formation of nanoparticle aggregates that are too large to traverse the smaller infiltration routes like the pores. Additionally, it has been observed that the $T_2$ relaxation time is highly sensitive to doping with low concentration (e.g., ppm levels) of oleophilic nanoparticles, which may advantageously be further cost savings to the methods described herein.

Examples of nanoparticles suitable for use in NMR methods described herein may include, but are not limited to, nanoparticles comprising at least one of iron oxide (e.g., magnetite and maghemite), bimetallic ferrite nanoparticles (e.g., $CoFe_2O_4$, $MnFe_2O_4$, and $NiFe_2O_4$), gadolinium oxide, erbium oxide, cerium oxide, manganese oxide, niobium oxide, manganese chloride, and the like, and any combination thereof.

Nanoparticles described herein may have any desired shape, which may include, but is not limited to, spherical, substantially spherical, ellipsoidal, substantially ellipsoidal (e.g., rice-shaped or prolate), elongate (e.g., rods, wires, tubes, or fibers), star-shaped (e.g., tripod, tetrapod, and so on), discus, faceted (e.g., crystalline or semi-crystalline), and the like, and any combination thereof.

The oleophilic nanoparticles described herein may have an average diameter (without inclusion of the oleophilic surface modification) ranging from about 1 nm to about 500 nm, including any subset therebetween (e.g., about 1 nm to about 150 nm, about 1 nm to about 50 nm, or about 3 nm to about 15 nm). Examples of oleophilic surface modifications may include, but are not limited to, $C_4$-$C_{30}$ alcohols, $C_4$-$C_{30}$ fatty acids, $C_4$-$C_{30}$ phosphonates, and the like, and any combination thereof, wherein the $C_4$-$C_{30}$ may be characterized by at least one selected from the group consisting of a straight chain, a branched chain, comprising an unsaturated C—C bond, comprising a cyclic group, comprising an aryl group, and the like, and any combination thereof. Specific examples may include, but are not limited to, octanol, nonanol, decanol, dodecanol, octylphenol, dodecylphenol, caprylic acid, capric acid, lauric acid, myristic acid, palmitic acid, steric acid, myristoleic acid, palmitoleic acid, sapienic acid, oleic acid, elaidic acid, vaccenic acid, linoleic acid, linoelaidic acid, erucic acid, octylphenol, nonylphenol, dodecylphenol, cetylphenol, and the like, and any combination thereof.

In some embodiments, oleophilic nanoparticles may be included in wellbore fluids described herein in an amount of about 0.002% to about 1% by weight of the oil-based wellbore fluid, including any subset therebetween (e.g., about 0.1% to about 1% or about 0.01% to about 0.5%).

In some embodiments, oil-based wellbore fluids, and corresponding oil-based filtrates, may comprise an oil base fluid and a plurality of oleophilic nanoparticles described herein. Examples of oil base fluids phase may include, but are not limited to, alkanes, olefins, aromatic organic compounds, cyclic alkanes, paraffins, diesel fluids, mineral oils, kerosene, desulfurized hydrogenated kerosenes, fuel oil, vegetable oil, and the like, and any combination thereof.

In some embodiments, the oil-based wellbore fluids may comprise an oil base fluid, a plurality of oleophilic nanoparticles, and at least one additive. Examples of additives may include, but are not limited to, salts, weighting agents, inert solids, fluid loss control agents, emulsifiers, dispersion aids, corrosion inhibitors, emulsion thinners, emulsion thickeners, viscosifying agents, gelling agents, surfactants, particulates, proppants, gravel particulates, lost circulation materials, foaming agents, gases, pH control additives, breakers, biocides, crosslinkers, stabilizers, chelating agents, scale inhibitors, gas hydrate inhibitors, mutual solvents, oxidizers, reducers, friction reducers, clay stabilizing agents, and the like, and any combination thereof. For example, the oil-based wellbore fluid may be a oil-based drilling fluid that comprises an oil base fluid, a plurality of oleophilic nanoparticles, and at least one additive like weighting agents, lost circulation materials, inert solids, and the like, and any combination thereof.

The ability to differentiate light oil from oil-based wellbore fluids and filtrates may be useful in a plurality of methods that utilize NMR measurement techniques downhole to ascertain properties of the subterranean formation and/or the formation fluid. Examples of methods that utilize NMR measurement techniques downhole include, but are not limited to, generating oil-based filtrate invasion profiles, measuring vug porosity, analyzing vug connectivity, detecting contamination of formation fluids by oil-based filtrates, and analyzing the near-wellbore formation for residual oil saturation, each described in more detail herein.

Invasion profiles provide information about the extent to which a wellbore fluid has invaded the near-wellbore portion of the subterranean formation. Wellbore fluid invasion is most prevalent before the additives in a wellbore fluid have formed a filter cake, e.g., during drilling operations.

Drilling a wellbore with an oil-based drilling fluid that comprises oleophilic nanoparticles described herein may advantageously provide for discrimination between the oil-based drilling fluid that has invaded the near-wellbore in the formation fluid, especially light oil, when analyzing NMR logging measurements. Some embodiments may involve drilling a wellbore penetrating a subterranean formation with a oil-based drilling fluid that comprises an oil base fluid and a plurality of oleophilic nanoparticles; performing a plurality of NMR measurements at a plurality of depths of investigation (DOI) of a near-wellbore portion of the subterranean formation; and producing an invasion profile of a oil-based drilling fluid filtrate into the near-wellbore portion of the subterranean formation based on the plurality of NMR measurements. As used herein, the term "depth of investigation" refers to a depth from the wellbore into the subterranean formation. Changing the DOI of an NMR measurement can be achieved by varying the transmitting frequency. This can be done with wireline post drilling and mud cake formation or during LWD.

In some instances, the oil base fluid of the oil-based drilling fluid may be miscible with the formation fluid or a portion thereof, which may act to dilute the oil-based drilling fluid filtrate and lower the concentration of the oleophilic nanoparticles, especially at the leading-edge of the oil-based drilling fluid filtrate. The magnitude of the change to the NMR property (e.g., reducing the $T_1$ relaxation time, reducing the $T_2$ relaxation time, and/or parameters relating thereto) is dependent on the concentration of the oleophilic nanoparticles, which can be used to derive an approximate concentration of the oil-based drilling fluid in the native oil-based formation fluid.

In some instances, the invasion profile may be utilized to identify portions of the wellbore to be isolated during production operations (e.g., thief zones or zones containing little oil), which may increase the efficiency and reduce the cost associated with hydrocarbon production. Accordingly, some embodiments may involve isolating a portion of the subterranean formation based on the invasion profile; and producing hydrocarbons from the subterranean formation.

In some instances, the invasion profile may be utilized to identify a sample of uncontaminated formation fluid. Then, the NMR measurements corresponding to the uncontaminated formation fluid may be utilized to derive properties of the formation fluid, e.g., viscosity, composition, gas-to-oil ratio (GOR), hydrogen index, and the like. As used herein, the term "uncontaminated formation fluid" refers to formation fluid having a concentration of wellbore fluid filtrate below a desired threshold, which may be ascertained by the concentration of oleophilic nanoparticles therein. The desired threshold may be an absolute threshold (e.g., about 5% to about 10%). In some instances, the desired threshold may be a delta threshold where a series of samples or data points are analyzed as a function of distance from the surface of the wellbore and the value of the NMR measurement changes by less than the delta threshold from sample to sample or data point to data point (e.g., less than about 5%, or, when plotted, e.g., as a function of pumping or recovery time, the value of the NMR measurement approaches an asymptote).

In some instances, it may be preferred to collect a sample of uncontaminated formation fluid for additional analysis outside the wellbore. Collection of uncontaminated formation fluid may involve extracting a plurality of near-wellbore fluid samples with an NMR wellbore tool and analyzing at least one NMR parameter of the near-wellbore fluid samples to identify and collect an uncontaminated formation fluid sample. In some embodiments, the samples may be portions of a continuous flow of formation fluids extracted by pumping from the surface, and the NMR wellbore tool may analyze the samples by plotting the NMR measurement as a function of time, which as described above may be used to determine when an uncontaminated formation fluid sample can be collected. Utilizing the nanoparticles as described above to determine when a sample comprises uncontaminated formation fluid may advantageously reduce the time and associated cost with this wellbore operation, which now is performed by pumping formation fluid for a preset time before collecting a sample and assumes that the sample collected comprises uncontaminated formation fluid. The use of nanoparticles provides a better measure of the contamination level of a oil-based wellbore filtrate in an oil-based formation fluid.

Some embodiments may involve drilling a wellbore penetrating a subterranean formation with a oil-based drilling fluid that comprises an oil base fluid and a plurality of oleophilic nanoparticles; extracting a plurality of near-wellbore fluid samples from the subterranean formation; measuring an NMR parameter of the near-wellbore fluid samples with an NMR wellbore tool; and collecting the near-wellbore fluid sample comprising an uncontaminated formation fluid.

In some instances, NMR methods may be useful in determining characteristics of the subterranean formation, e.g., vug porosity and vug connectivity. As used herein, the term "vug" refers to large sized pores in the subterranean formation that are generally smaller than the microfractures in the subterranean formation. As used herein, the term "vug porosity" refers to the vug contribution to the total porosity of the subterranean formation. As used herein, the term "vug connectivity" refers to the extent and type of fluid communication between individual vugs.

Because the NMR relaxation times of wetting phase fluid in pore space are approximately proportional to the pore size, the large pores (vugs) have the long relaxation times that may substantially overlap with that of the light oils. Therefore, when NMR relaxation time distributions show some porosity associated with long $T_1$ and/or $T_2$, it is not clear whether this signal contribution is from light oil or vug porosity.

In some embodiments, ascertaining vug porosity may involve drilling a wellbore penetrating a subterranean formation; measuring a first porosity distribution for the subterranean formation with a first NMR wellbore tool; reaming a wellbore surface, thereby yielding a reamed wellbore; introducing a wellbore fluid into the reamed wellbore, the wellbore fluid comprising an oil base fluid and a plurality of oleophilic nanoparticles; measuring a second porosity distribution of the subterranean formation with a second NMR wellbore tool; and determining a vug porosity of the subterranean formation based on a comparison of the first porosity distribution and the second porosity distribution. When ascertaining vug porosity, it may be desirable that the invading filtrate is allowed to pass through the formation matrix to reach the vugs, thus the nanoparticle size is preferably small, e.g., less than the pore throat dimension within the matrix. Since typical pore throat size is of the order of microns, a nanoparticle size one to two orders of magnitude smaller than that is desirable; and minimal aggregation within the formation is preferred. In some instances, measuring the first porosity and drilling may occur simultaneously, e.g., with NMR wellbore tools like logging-while-drilling (LWD) or measurement-while-drilling (MWD) tools.

In some embodiments, ascertaining vug porosity may involve drilling a wellbore penetrating a subterranean formation with an oil-based drilling fluid comprising an oil base fluid and a plurality of oleophilic nanoparticles; measuring a first porosity distribution for the subterranean formation with a first NMR wellbore tool; measuring a second porosity distribution of the subterranean formation with a second NMR wellbore tool; and determining a vug porosity of the subterranean formation based on a comparison of the first porosity distribution and the second porosity distribution. In some instances, the first and second NMR wellbore tools may be the same. In some instances, the first NMR wellbore tool may be an NMR-LWD wellbore tool. In some instances, depending on the NMR wellbore tool (e.g., depth of signal penetration) and composition of the oil-based wellbore fluid, an NMR-LWD may be sufficiently close to the drill-bit that minimal drilling fluid has infiltrated the subterranean formation, thereby allowing for measuring a first porosity distribution with minimal contribution from a filtrate.

Vug connectivity can be classified as ranging between separate vugs, where individual vugs are fluidly connected via the porosity of the subterranean formation matrix, and touching vugs, where individual vugs are hydraulically connected by larger pores or microfractures allowing for fluid may readily travel between vugs.

Methods of ascertaining vug connectivity may utilize larger nanoparticles, or nanoparticle aggregates, that do not readily traverse the porosity of the subterranean formation that can readily traverse larger pores and microfractures. In some instances, the oleophilic nanoparticles described herein may be designed for minimal aggregation as the oil-based wellbore fluid circulates through the wellbore and significant aggregation between the filter cake and the subterranean formation. The design of such oleophilic nanoparticles may be achieved, for example, with oleophilic surface modifications that comprise shorter (e.g., $C_4$-$C_8$), saturated alkyl chains, with oleophilic surface modifications that comprise a group that binds less effectively to the surface of the nanoparticle (e.g., alcohols have a lower binding strength than carboxylic acids, which may have a lower binding strength than phosphonates). Further, the aggregation state of the oleophilic nanoparticles may be enhanced by the motion of the fluid thereabout. For example, the flowing fluid in the wellbore (e.g., turbid or laminar depending on the conditions) may mitigate aggregation, while the relatively static fluid between the filter cake and the subterranean formation may allow for increased aggregation.

Aggregation of the oleophilic nanoparticles may allow for the formation of nanoparticle clusters having diameters larger than the pore throat size of the subterranean formation. However, the nanoparticle cluster diameter may be sufficiently small to traverse the larger pores and microfractures that connect vugs. As such, NMR logging methods described herein may be used to ascertain vug connectivity.

Some embodiments may involve introducing an oil-based wellbore fluid into a wellbore penetrating a subterranean formation, the oil-based wellbore fluid comprising an oil-based fluid and a plurality of oleophilic nanoparticles; forming a plurality of nanoparticle aggregates between a filter cake and at least a portion of the subterranean formation, the nanoparticle aggregates comprising the oleophilic nanoparticles; performing a plurality of NMR measurements at the portion of the subterranean formation; and determining a vug connectivity based on the plurality of NMR measurements.

Some embodiments may involve introducing an oil-based wellbore fluid into a wellbore penetrating a subterranean formation, the oil-based wellbore fluid comprising an oil-based fluid and a plurality of oleophilic nanoparticles; forming a plurality of nanoparticle aggregates between a filter cake and at least a portion of the subterranean formation, the nanoparticle aggregates comprising the oleophilic nanoparticles; performing a plurality of NMR measurements at a plurality of DOI at the portion of the subterranean formation; and producing an invasion profile of the nanoparticle aggregates based on the plurality of NMR measurements.

In some instances, the vug porosity and/or vug connectivity may be utilized to identify portions of the wellbore to be isolated during production operations (e.g., zones with little to no vug porosity and/or vug connectivity), which may increase the efficiency and reduce the cost associated with hydrocarbon production. Accordingly, some embodiments may involve isolating a portion of the subterranean formation based on at least one of the vug porosity, the vug connectivity, the invasion profile of nanoparticle aggregates, and any combination thereof; and producing hydrocarbons from the subterranean formation.

In some instances, NMR methods may be useful in determining characteristics of a subterranean formation having an existing wellbore that has been used for hydrocarbon production. Subterranean formations often have hydrocarbon resources trapped therein in a plurality of ways. After the primary and secondary production removes the readily accessible hydrocarbons, some subterranean formations have residual oil disposed therein. As used herein, the term "residual oil" refers to hydrocarbons that do not move with fluid flow through the subterranean formation under normal conditions, e.g., in primary and secondary recovery operations or in invasion operations.

NMR logging methods can be used for identifying residual oil and determining the concentration thereof.

While residual oil saturation measurements are more commonly performed with water-based contrast agents in water-based wellbore fluids, many types of wells have adverse reactions with water-based wellbore fluids (e.g., dehydration formations, high-temperature reservoirs, and swelling clay-rich formations). Accordingly, oil-based wellbore fluid may preferably be utilized. Some embodiments may involve introducing a wellbore fluid comprising an oil base fluid and a plurality of oleophilic nanoparticles described herein into a subterranean formation comprising residual oil that comprises light oil; performing NMR measurements on a near-wellbore portion of the subterranean formation; and determining the residual oil saturation based on the NMR measurements. In some instances, determining the residual oil saturation may involve integrating the portions of the NMR measurements corresponding to the residual oil, e.g., light oil. The use of the oleophilic nanoparticles in the wellbore fluid gives the wellbore fluid a significantly different value for a given NMR parameter, thereby providing for fluid differentiation.

After determining the residual oil saturation, some embodiments may involve recovering the residual oil. This may optionally involve isolation of portions of the wellbore with high levels of residual oil saturation, which may increase the efficiency and reduce the cost associated with residual oil production.

To facilitate a better understanding of the present invention, the following examples of preferred or representative embodiments are given. In no way should the following examples be read to limit, or to define, the scope of the invention.

EXAMPLES

Example 1

Iron oxide oleophilic nanoparticles (10 nm iron oxide nanoparticles having a hydrophobic surface modification of oleic acid) were suspended in light oil at a weight % concentration of about 1000 ppm. The $T_2$ relaxation time of the light oil with and without the nanoparticle was measured, FIG. 1.

This example illustrates that the oleophilic nanoparticles change the value of the NMR parameter ($T_2$ relaxation time) and provide for a sharp peak, which will further enhance the identification of fluids comprising the oleophilic nanoparticles.

Example 2

Figure 2:
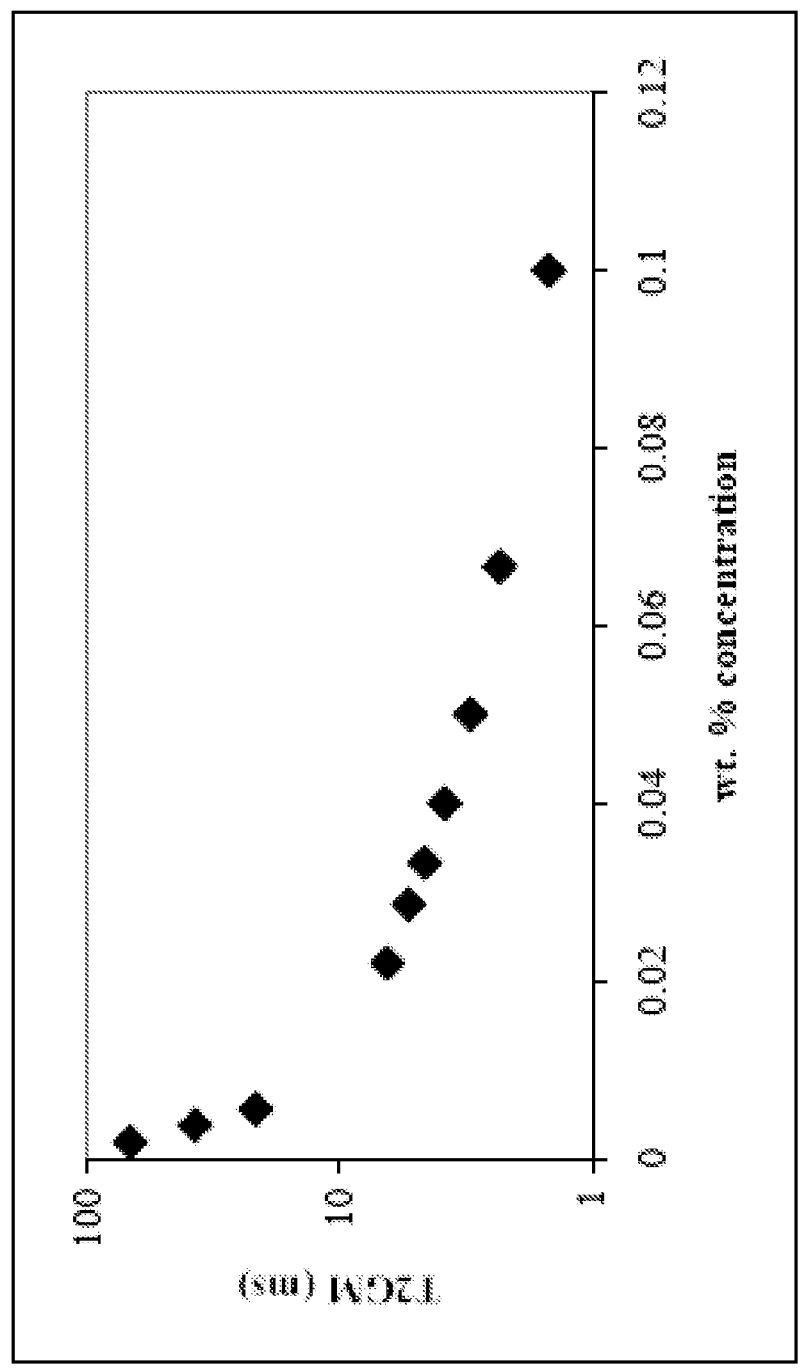
FIG. 2 provides a $T_2$ relaxation time vs concentration plot for light oil samples doped with varying concentrations of oleophilic nanoparticles.

Iron oxide oleophilic nanoparticles (10 nm iron oxide nanoparticles having a hydrophobic surface modification of oleic acid) were suspended in light oil at a plurality of weight % concentrations. The $T_2$ relaxation time of the samples were analyzed, FIG. 2.

This example illustrates that the change in the value of the NMR parameter ($T_2$ relaxation time) is dependent on the concentration of the oleophilic nanoparticles. In addition, this example demonstrates the extraordinary sensitivity of the $T_2$ relaxation time to micro-doping of light oil, which implies the cost effectiveness of oleophilic nanoparticles. Accordingly, the value of the NMR parameter can be an indicator of dilution due to mixing of a wellbore fluid filtrate with a formation fluid.

Example 3

Figure 3:
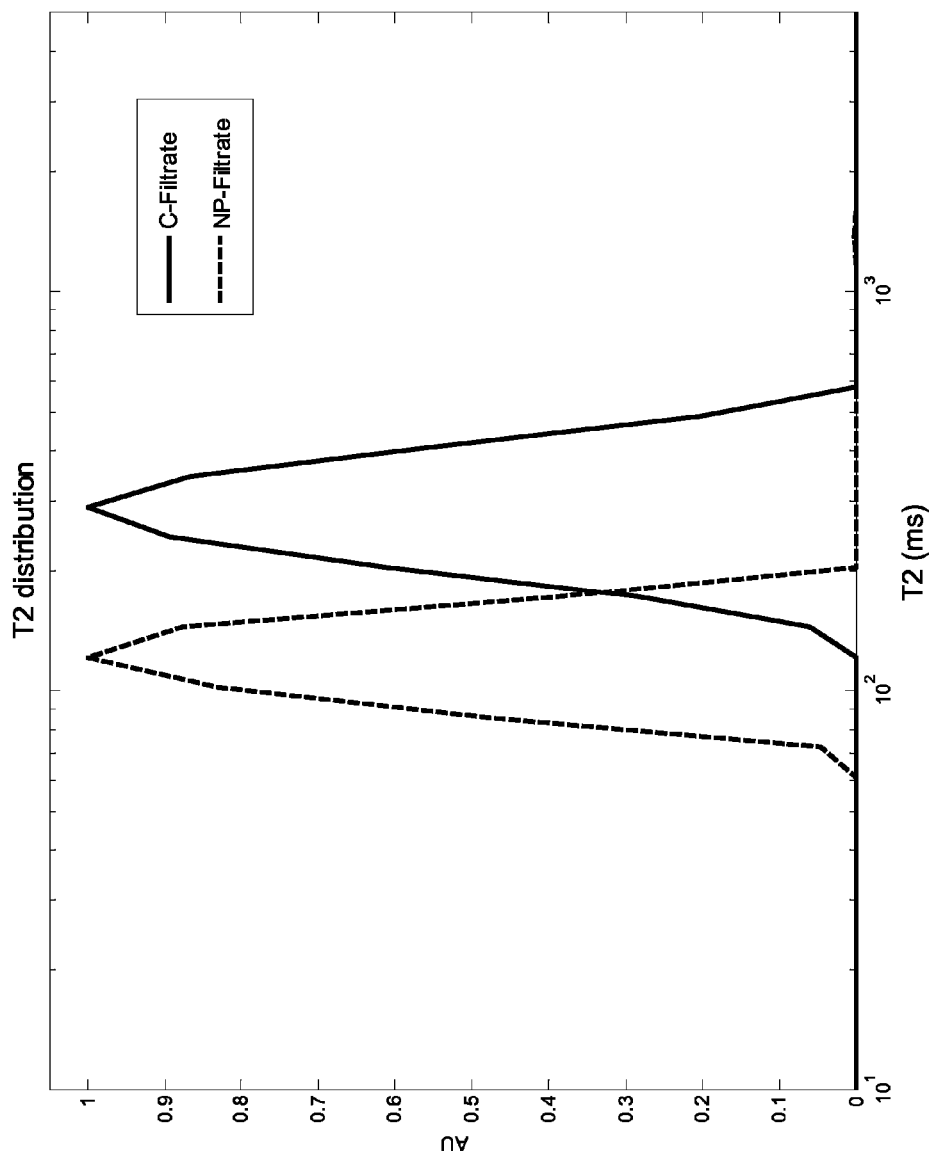
FIG. 3 provides a $T_2$ relaxation time plot for filtrates of oil-based drilling fluids obtained from a mud press with and without oleophilic nanoparticles.

Two samples of oil-based drilling fluids were prepared, a control without nanoparticles and a second with oleophilic nanoparticles (10 nm iron oxide nanoparticles having a hydrophobic surface modification of oleic acid). A mud press test was performed on the oil-based drilling fluid samples. The resultant filtrate was analyzed by NMR with the $T_2$ relaxation time distributions of the filtrate of the oil-based drilling fluid without nanoparticles ("C-filtrate") and the filtrate of the oil-based drilling fluid with nanoparticles ("NP-filtrate") provided in FIG. 3. The $T_2$ of the NP-filtrate is approximately 3 times smaller than the C-filtrate. This example demonstrates the applicability of oil-based wellbore fluids comprising oleophilic nanoparticles in the methods described herein.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present invention. The invention illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

The invention claimed is:

1. A method comprising:
    drilling a wellbore penetrating a subterranean formation using an oil-based drilling fluid that comprises an oil base fluid and a plurality of ferromagnetic oleophilic nanoparticles;
    performing a plurality of nuclear magnetic resonance (NMR) measurements at a plurality of depths of investigation (DOI) of a near-wellbore portion of the subterranean formation; and
    producing an invasion profile of an oil-based drilling fluid filtrate into the near-wellbore portion of the subterranean formation based on the plurality of NMR measurements.

2. The method of claim 1, wherein the oleophilic nanoparticles comprise at least one selected from the group consisting of iron oxide, bimetallic ferrite nanoparticles, gadolinium oxide, erbium oxide, cerium oxide, manganese oxide, niobium oxide, manganese chloride, and any combination thereof.

3. The method of claim 1, wherein the oleophilic nanoparticles have an average diameter of about 1 nm to about 500 nm.

4. The method of claim 1, wherein the oleophilic nanoparticles comprise a hydrophobic surface modification comprising at least one selected from the group consisting of a $C_4$-$C_{30}$ alcohol, a $C_4$-$C_{30}$ fatty acid, a $C_4$-$C_{30}$ phosphonate, and any combination thereof, wherein the $C_4$-$C_{30}$ is characterized by at least one selected from the group consisting of a straight chain, a branched chain, comprising an unsaturated C—C bond, comprising a cyclic group, comprising an aryl group, and any combination thereof.

5. The method of claim 1, wherein the oleophilic nanoparticles comprise a hydrophobic surface modification comprising at least one selected from the group consisting of octanol, nonanol, decanol, dodecanol, octylphenol, dodecylphenol, caprylic acid, capric acid, lauric acid, myristic acid, palmitic acid, steric acid, myristoleic acid, palmitoleic acid, sapienic acid, oleic acid, elaidic acid, vaccenic acid, linoleic acid, linoelaidic acid, erucic acid, octylphenol, nonylphenol, dodecylphenol, cetylphenol, and any combination thereof.

6. The method of claim 1, wherein the oleophilic nanoparticles are present in the oil-based drilling fluid in an amount of about 0.01% to about 1% by weight of the oil-based drilling fluid.

7. The method of claim 1, wherein the NMR measurements are of at least one NMR parameter selected from the group consisting of a $T_1$ relaxation time, a $T_2$ relaxation time, a parameter relating thereto, and any combination thereof.

8. The method of claim 1 further comprising:
isolating a portion of the subterranean formation based on the invasion profile.

9. The method of claim 1 further comprising:
producing a hydrocarbon from the subterranean formation.

10. The method of claim 1 further comprising:
identifying a portion of the near-wellbore comprising an uncontaminated formation fluid; and
deriving a property of the uncontaminated formation fluid based on the NMR measurements corresponding to the uncontaminated formation fluid.

11. A method comprising:
drilling a wellbore penetrating a subterranean formation using an oil-based drilling fluid that comprises an oil base fluid and a plurality of ferromagnetic oleophilic nanoparticles;
extracting a plurality of near-wellbore fluid samples from the subterranean formation;
measuring a nuclear magnetic resonance (NMR) parameter of the near-wellbore fluid samples with an NMR wellbore tool; and
collecting the near-wellbore fluid sample comprising an uncontaminated formation fluid.

12. The method of claim 11, wherein the oleophilic nanoparticles comprise at least one selected from the group consisting of iron oxide, bimetallic ferrite nanoparticles, gadolinium oxide, erbium oxide, cerium oxide, manganese oxide, niobium oxide, manganese chloride, and any combination thereof.

13. The method of claim 11, wherein the oleophilic nanoparticles have an average diameter of about 1 nm to about 500 nm.

14. The method of claim 11, wherein the oleophilic nanoparticles comprise a hydrophobic surface modification comprising at least one selected from the group consisting of a $C_4$-$C_{30}$ alcohol, a $C_4$-$C_{30}$ fatty acid, a $C_4$-$C_{30}$ phosphonate, and any combination thereof, wherein the $C_4$-$C_{30}$ is characterized by at least one selected from the group consisting of a straight chain, a branched chain, comprising an unsaturated C—C bond, comprising a cyclic group, comprising an aryl group, and any combination thereof.

15. The method of claim 11, wherein the oleophilic nanoparticles comprise a hydrophobic surface modification comprising at least one selected from the group consisting of octanol, nonanol, decanol, dodecanol, octylphenol, dodecylphenol, caprylic acid, capric acid, lauric acid, myristic acid, palmitic acid, steric acid, myristoleic acid, palmitoleic acid, sapienic acid, oleic acid, elaidic acid, vaccenic acid, linoleic acid, linoelaidic acid, erucic acid, octylphenol, nonylphenol, dodecylphenol, cetylphenol, and any combination thereof.

16. The method of claim 11, wherein the oleophilic nanoparticles are present in the oil-based drilling fluid in an amount of about 0.002% to about 1% by weight of the oil-based drilling fluid.

17. The method of claim 11, wherein the NMR parameter is at least one selected from the group consisting of a $T_1$ relaxation time, a $T_2$ relaxation time, a parameter relating thereto, and any combination thereof.

18. A method comprising:
introducing a wellbore fluid comprising an oil base fluid and a plurality of ferromagnetic oleophilic nanoparticles into a subterranean formation comprising residual oil that comprises light oil;
performing nuclear magnetic resonance (NMR) measurements on a near-wellbore portion of the subterranean formation; and
determining the residual oil saturation based on the NMR measurements.

19. The method of claim 18, wherein the oleophilic nanoparticles comprise at least one selected from the group consisting of iron oxide, bimetallic ferrite nanoparticles, gadolinium oxide, erbium oxide, cerium oxide, manganese oxide, niobium oxide, manganese chloride, and any combination thereof.

20. The method of claim 18, wherein the oleophilic nanoparticles comprise a hydrophobic surface modification comprising at least one selected from the group consisting of octanol, nonanol, decanol, dodecanol, octylphenol, dodecylphenol, caprylic acid, capric acid, lauric acid, myristic acid, palmitic acid, steric acid, myristoleic acid, palmitoleic acid, sapienic acid, oleic acid, elaidic acid, vaccenic acid, linoleic acid, linoelaidic acid, erucic acid, octylphenol, nonylphenol, dodecylphenol, cetylphenol, and any combination thereof.

* * * * *